(12) United States Patent
Kaufman

(10) Patent No.: US 11,896,426 B2
(45) Date of Patent: Feb. 13, 2024

(54) DUAL-MODE ULTRASONIC ASSESSMENT OF BONE

(71) Applicant: Jonathan Joseph Kaufman, Brooklyn, NY (US)

(72) Inventor: Jonathan Joseph Kaufman, Brooklyn, NY (US)

( * ) Notice: Subject to any disclaimer, the term of this patent is extended or adjusted under 35 U.S.C. 154(b) by 520 days.

(21) Appl. No.: 16/703,481

(22) Filed: Dec. 4, 2019

(65) Prior Publication Data

US 2020/0170616 A1  Jun. 4, 2020

Related U.S. Application Data

(60) Provisional application No. 62/775,144, filed on Dec. 4, 2018.

(51) Int. Cl.
| | |
|---|---|
| *A61B 8/00* | (2006.01) |
| *A61B 8/08* | (2006.01) |
| *G06T 7/00* | (2017.01) |

(52) U.S. Cl.
CPC .......... *A61B 8/0875* (2013.01); *A61B 8/4281* (2013.01); *A61B 8/5207* (2013.01); *G06T 7/0012* (2013.01); *G06T 2207/10132* (2013.01); *G06T 2207/30008* (2013.01)

(58) Field of Classification Search
CPC ... A61B 8/0875; A61B 8/4281; A61B 8/5207; G06T 7/0012; G06T 2207/10132; G06T 2207/30008
See application file for complete search history.

(56) References Cited

U.S. PATENT DOCUMENTS

| | | | |
|---|---|---|---|
| 2010/0030080 A1* | 2/2010 | Suetoshi | A61B 5/4509 600/449 |
| 2015/0211844 A1* | 7/2015 | Cretin | G01B 17/02 702/171 |

OTHER PUBLICATIONS

Kaufman, Jonahan J. et al. Abstract "A New Dual-Mode Ultrasonic Technique for Assessing Cortical Bone," 142 Journal of the Acoustical Society of America No. 4, Pt. 2 p. 2565 (Oct. 2017).

Kaufman, Johnathan J. et al. "Dual-Mode Ultrasound for Assessing Cortical Bone" 174th Meeting of Acoustical Society of America (Dec. 5, 2017).

(Continued)

*Primary Examiner* — Shahdeep Mohammed
*Assistant Examiner* — Adam D. Kolkin
(74) *Attorney, Agent, or Firm* — Reising Ethington P.C.

(57) ABSTRACT

A system and method for non-invasive and quantitative assessment of the status of bone tissue in a bony member within a living organism are provided. In one embodiment, the system includes a transducer and a controller that causes the transducer to generate a pair of axial ultrasound signals traveling in opposite directions along a longitudinal axis of the bony member and a radial ultrasound signal traveling towards and into the bony member. The transducer receives multiple portions of each of the axial ultrasound signals and multiple portions of the radial ultrasound signal reflected by the bony member and generates axial and pulse-echo output signals in response. The controller processes the axial and pule-echo output signals to obtain an axial transmission time delay and a pulse-echo time delay, respectively, and generates an estimate of a characteristic of the bone tissue responsive to the axial-transmission and pulse-echo time delays.

29 Claims, 7 Drawing Sheets

(56) References Cited

OTHER PUBLICATIONS

Kaufmann, Jonathan. J. et al. "Ultrasound Assessment of Bone," 8 Journal of Bone Mineral Research No. 5, pp. 517-525 (1993).
Schousboe, J.T. et al. "Prediction of Hip Osteoporosis by DXA Using a Novel Pulse-Echo Ultrasound Device," 28 Osteoporosis International pp. 85-93 (2017).
Siffert R.S. et al. "Ultrasonic Bone Assessment: The Time Has Come," 40 Bone pp. 5-8 (2007).
Vallet, Quentin et al., "In Vivo Characterization of Cortical Bone Using Guided Waves Measured by Axial Transmission," 63 IEEE Transactions on Ultrasonics, Ferroelectrics and Frequency Control No. 9 pp. 1361-1371 (Sep. 2016).

\* cited by examiner

| N = 11 (Number of subjects) | Mean (SD) | Min-Max |
|---|---|---|
| Age [Years] | 46 (17) | 21-72 |
| Race 91% White 9% Asian | | |
| Sex (46% female) | | |
| Height [cm] | 162 (9) | 150-175 |
| Weight [kg] | 59 (11) | 47-77 |
| $\tau_{P\text{-}E}$ [µs] | 1.49 (0.46) | 0.82-2.42 |
| $v_a$ [mm/µs] | 3.47 (0.13) | 3.28 – 3.70 |

FIG. 6

DUAL-MODE ULTRASONIC ASSESSMENT OF BONE

CROSS-REFERENCE TO RELATED APPLICATIONS

This application claims priority to U.S. Provisional Patent Application No. 62/775,144 filed Dec. 4, 2018, the entire disclosure of which is incorporated herein by reference.

BACKGROUND OF THE INVENTION a. Field of the Invention

This invention relates to a system and method for non-invasive and quantitative assessment of the status of bone tissue in a bony member within a living organism. In particular, the invention relates to a system and method that evaluate a characteristic of bone tissue responsive to both the transit time for ultrasound signals moving through the bone tissue along a longitudinal axis of a bony member and the transit time for ultrasound signals reflected from the bone tissue radially away from the longitudinal axis of the bony member.

b. Background Art

Osteoporotic fractures are a major public health problem which is typically diagnosed using x-ray densitometry (DXA). See Bonnick S. L., "Bone Densitometry in Clinical Practice," (2004), the entire disclosure of which is incorporated herein by reference. DXA, however, is not able to accurately predict who will and will not suffer an osteoporotic fracture. One alternative to DXA is ultrasound, which is viewed as having the potential to better characterize fracture risk. See Kaufman, J. J. et al. "Ultrasound Assessment of Bone," 8 Journal of Bone and Mineral Research No. 5 pp. 517-25 (1993), Siffert, R. S. et al. "Ultrasonic Bone Assessment: 'The Time Has come.'" 40 Bone No. 1, pp. 5-8 (2007), U.S. Pat. No. 7,862,510, and Stein E. M. et al. "Clinical Assessment of the ⅓ Radius Using a New Desktop Ultrasonic Bone Densitometer," 39 Ultrasound in Medicine & Biology No. 3 pp. 388-395 (2013), the entire disclosures of which are incorporated herein by reference. Ultrasound also provides several advantages relative to DXA including portability, cost and freedom from exposure to radiation. Conventional systems and methods employing ultrasound for assessment of bone tissue transmit ultrasound signals towards bone tissue and then either receive signals passing through the bone tissue or signals reflected from the bone tissue. Each type of system can provide useful information about characteristics of the bone tissue, but the information provided by each system is different and subject to certain limitations. In particular while both types of system are dependent on cortical thickness, through transmission is also dependent on bone material properties (e.g., intracortical porosity, degree of bone mineralization) while reflected ultrasound is also dependent on ultrasound velocity. Existing systems may therefore fail to provide accurate assessments of bone tissue depending on various factors associated with a subject.

The inventor herein has recognized a need for a system and method for non-invasive and quantitative assessment of the status of bone tissue in a bony member within a living organism that will overcome one or more of the above-identified deficiencies.

BRIEF SUMMARY OF THE INVENTION

This invention relates to a system and method for non-invasive and quantitative assessment of the status of bone tissue in a bony member within a living organism. In particular, the invention relates to a system and method that evaluate a characteristic of bone tissue responsive to both the transit time for ultrasound signals moving through the bone tissue along a longitudinal axis of a bony member and the transit time for ultrasound signals reflected from the bone tissue radially away from the longitudinal axis of the bony member.

A system for non-invasive and quantitative assessment of the status of bone tissue in a bony member within a living organism in accordance with one embodiment of the invention includes a transducer configured for coupling to skin disposed over the bony member and a controller coupled to the transducer. The controller is configured to generate a first control signal causing the transducer to generate a first axial ultrasound signal from the transducer towards and into the bony member wherein portions of the first axial ultrasound signal travel along a longitudinal axis of the bony member in a first axial direction and to receive first and second portions of the first axial ultrasound signal at a first pair of acoustic elements of the transducer after the first and second portions of the first axial ultrasound signal have exited the bony member and generate a first pair of axial output signals in response. The controller is further configured to process the first pair of axial output signals to obtain an axial transmission time delay. The controller is further configured to generate a third control signal causing the transducer to generate a first radial ultrasound signal from the transducer towards and into the bony member wherein portions of the first radial ultrasound signal are reflected by the bony member in a direction away from the longitudinal axis of the bony member and receive first and second portions of the first radial ultrasound signal after reflection by the bony member and generate a pulse-echo output signal in response. The controller is further configured to process the pulse-echo output signal to obtain a pulse-echo time delay and generate an estimate of a characteristic of the bone tissue responsive to the axial-transmission time delay and the pulse-echo time delay.

A system for non-invasive and quantitative assessment of the status of bone tissue in a bony member within a living organism in accordance with another embodiment of the invention includes a first transducer configured for coupling to skin disposed over the bony member, a second transducer configured for coupling to skin disposed over the bony member, and a controller coupled to the first and second transducers. The controller is configured to generate a first control signal causing the first transducer to generate a first axial ultrasound signal from the first transducer towards and into the bony member wherein portions of the first axial ultrasound signal travel along a longitudinal axis of the bony member in a first axial direction and receive first and second portions of the first axial ultrasound signal at a first pair of acoustic elements of the first transducer after the first and second portions of the first axial ultrasound signal have exited the bony member and generate a first pair of axial output signals in response. The controller is further configured to process the first pair of axial output signals to obtain an axial transmission time delay. The controller is further configured to generate a third control signal causing the second transducer to generate a first radial ultrasound signal from the second transducer towards and into the bony member wherein portions of the first radial ultrasound signal are reflected by the bony member in a direction away from the longitudinal axis of the bony member and receive first and second portions of the first radial ultrasound signal after reflection by the bony member and generate a pulse-echo output signal in response. The controller is further configured to process the pulse-echo output signal to obtain a pulse-echo time delay and generate an estimate of a characteristic of the bone tissue responsive to the axial-transmission time delay and the pulse-echo time delay.

A method for non-invasive and quantitative assessment of the status of bone tissue in a bony member within a living organism in accordance with one embodiment of the invention includes the step of acoustically coupling a transducer to skin disposed over the bony member. The method further includes the steps of generating a first axial ultrasound signal from the transducer towards and into the bony member wherein portions of the first axial ultrasound signal travel along a longitudinal axis of the bony member in a first axial direction and receiving first and second portions of the first axial ultrasound signal at a first pair of acoustic elements of the transducer after the first and second portions of the first axial ultrasound signal have exited the bony member and generating a first pair of axial output signals in response. The method further includes the step of processing the first pair of axial output signals to obtain an axial transmission time delay. The method further includes the steps of generating a first radial ultrasound signal from the transducer towards and into the bony member wherein portions of the first radial ultrasound signal are reflected by the bony member in a direction away from the longitudinal axis of the bony member and receiving first and second portions of the first radial ultrasound signal after reflection by the bony member and generating a pulse-echo output signal in response. The method further includes the steps of processing the pulse-echo output signal to obtain a pulse-echo time delay and generating an estimate of a characteristic of the bone tissue responsive to the axial-transmission time delay and the pulse-echo time delay.

A method for non-invasive and quantitative assessment of the status of bone tissue in a bony member within a living organism in accordance with another embodiment of the invention includes acoustically coupling a first transducer to skin disposed over the bony member. The method further includes the steps of generating a first axial ultrasound signal from the first transducer towards and into the bony member wherein portions of the first axial ultrasound signal travel along a longitudinal axis of the bony member in a first axial direction and receiving first and second portions of the first axial ultrasound signal at a first pair of acoustic elements of the first transducer after the first and second portions of the first axial ultrasound signal have exited the bony member and generating a first pair of axial output signals in response. The method further includes the step of processing the first pair of axial output signals to obtain an axial transmission time delay. The method further includes the step of acoustically coupling a second transducer to skin disposed over the bony member. The method further includes the steps of generating a first radial ultrasound signal from the second transducer towards and into the bony member wherein portions of the first radial ultrasound signal are reflected by the bony member in a direction away from the longitudinal axis of the bony member and receiving first and second portions of the first radial ultrasound signal after reflection by the bony member and generating a pulse-echo output signal in response. The method further includes the steps of processing the pulse-echo output signal to obtain a pulse-echo time delay and generating an estimate of a characteristic of the bone tissue responsive to the axial-transmission time delay and the pulse-echo time delay.

A method for non-invasive and quantitative assessment of the status of bone tissue in a bony member within a living organism in accordance with another embodiment of the invention includes acoustically coupling a transducer to skin disposed over the bony member. The method further includes the steps of generating a first axial-ultrasound signal in the bony member along a first axial direction to obtain a first pair of axial-ultrasound output signals, and generating a second axial-ultrasound signal in the bony member along a second axial direction, wherein the second axial direction is opposite to the first axial direction, to obtain a second pair of axial-ultrasound output signals. The method further includes the step of processing the first pair of axial-ultrasound output signals and the second pair of axial-ultrasound output signals, to obtain an axial-transmission time delay. The method further includes the steps of generating an ultrasound signal and directing the ultrasound signal from the transducer radially through the bone tissue to obtain a pulse-echo output signal and processing the pulse-echo output signal to obtain a pulse-echo time delay. The method further includes the step of generating an estimate of a characteristic of the bone tissue responsive to both the axial-transmission time delay and the pulse-echo time delay.

A system and method for non-invasive and quantitative assessment of the status of bone tissue in a bony member within a living organism in accordance with the present teachings are advantageous relative to conventional systems and methods because the inventive system and method use multiple modes of ultrasound interrogation to provide the most accurate information on both bone quality and cortical thickness thereby providing an improved assessment of bone strength and fracture risk. In this manner, the system and method will allow primary care physicians to better assess fracture risk to reduce under-diagnosis of osteoporosis and thereby reduce fragility fractures and associated morbidities.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 6 is a table summarizing the results of testing of a system and method or non-invasive and quantitative assessment of the status of bone tissue in a bony member in accordance with the present teachings.

DETAILED DESCRIPTION OF EMBODIMENTS OF THE INVENTION

Figure 1:
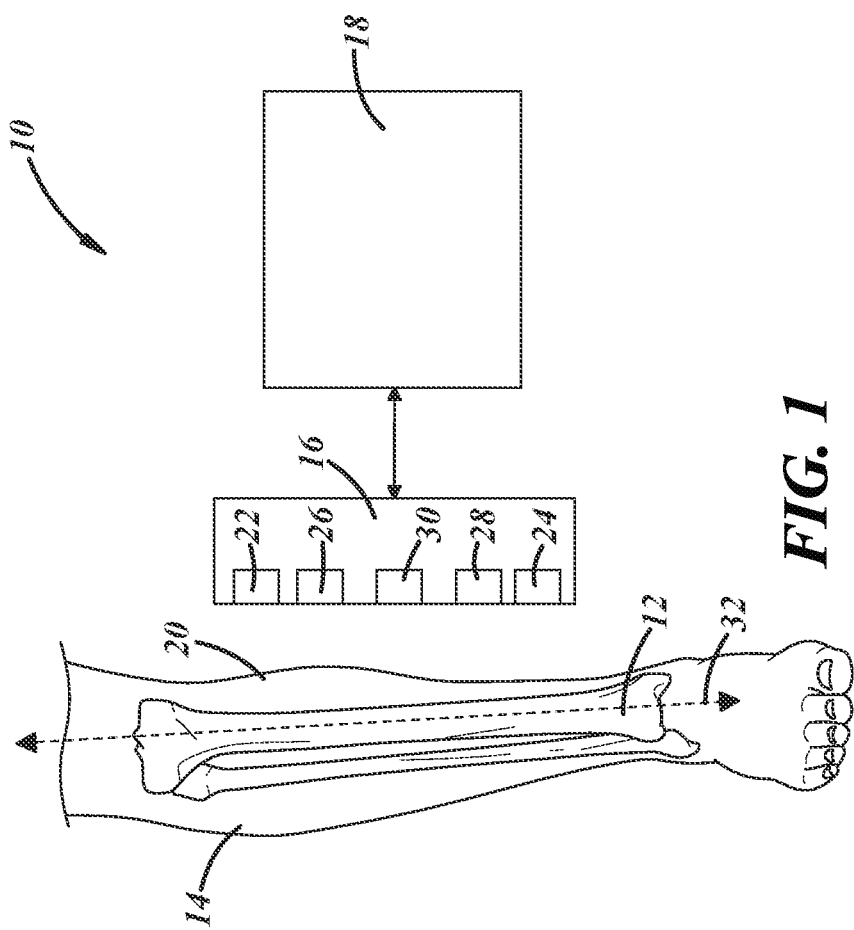
FIG. 1 is a diagrammatic view of a system for non-invasive and quantitative assessment of the status of bone tissue in a bony member within a living organism in accordance with one embodiment of the present teachings.

Referring now to the drawings wherein like reference numerals are used to identify identical components in the various views, FIG. 1 illustrates one embodiment of a system 10 for non-invasive and quantitative assessment of the status of bone tissue in a bony member 12 within a living organism 14. In one embodiment, the living organism 14 comprises a human being and the bony member 12 comprises a tibia. It should be understood, however, that the system and method described herein could be used on a wide variety of living organisms including all types of vertebrates and on a variety of bony members within those living organisms including, but not limited to, the radius, ulna and humerus bones. The system 10 includes an ultrasound transducer 16 and a controller 18.

Figure 2C:
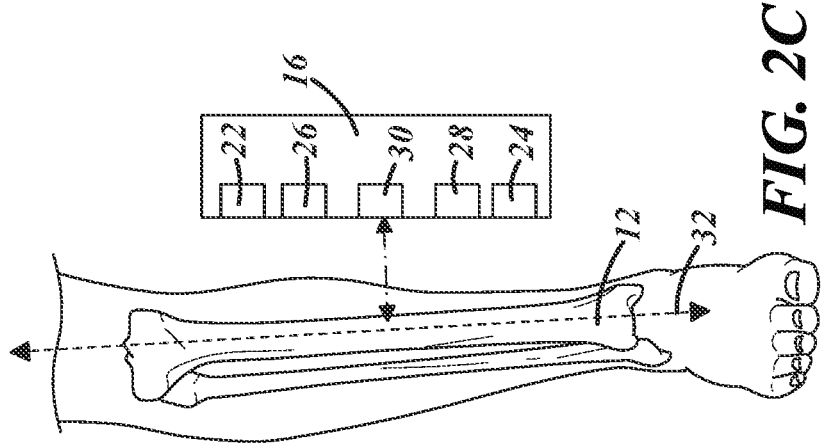
FIGS. 2A-2C are diagrammatic views of portions of the system of FIG. 1 illustrating the transmission and receipt of various ultrasound signals by the transducer of the system of FIG. 1.
Figure 2B:
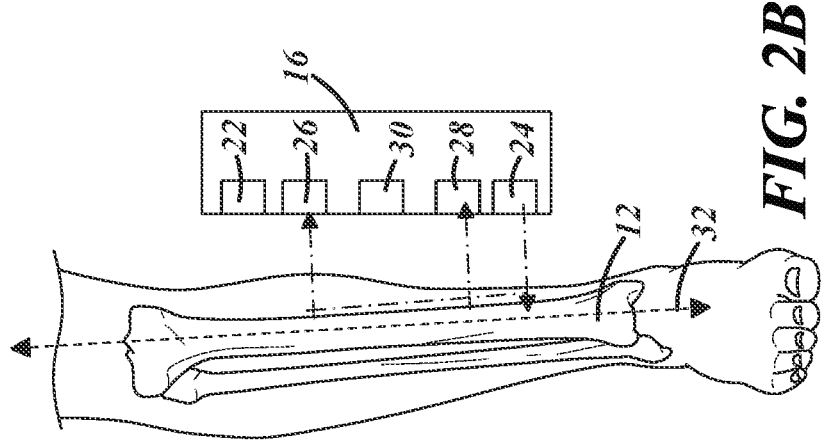
Figure 2A:
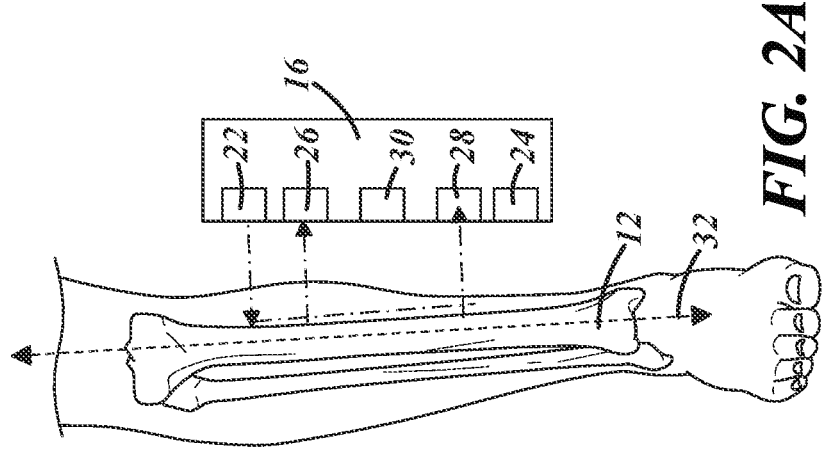

Transducer 16 is provided to transmit and receive, respectively, ultrasound signals. Transducer 16 is configured for coupling to skin 20 disposed over the bony member 12. In one embodiment where bony member 12 comprise a tibia, transducer 16 is located at the mid-shaft tibia at the anterior-medial aspect of the mid-shaft tibia. In the illustrated embodiment, transducer 16 includes five separate acoustic elements 22, 24, 26, 28, 30. Elements 22 and 24 are configured to transmit ultrasound signals towards and into the bony member 12 that travel in a substantially axial direction along a longitudinal axis 32 of bony member 12. As used herein a "substantially axial direction" means that the signals travel in a direction that is nearer to being parallel to axis 32 than to being parallel to a line extending perpendicular to axis 32. Referring to FIG. 2A, at least portions of the signals generated by element 22 travel along axis 32 in one axial direction. Referring to FIG. 2B, at least portions of the signals generated by element 24 travel along axis 32 in the opposite axial direction. Referring to FIGS. 2A-2B, elements 26, 28 are configured to receive different portions of the ultrasound signal generated by elements 22, 24 after those portions exit bony member 12. Elements 26, 28 together generate a pair of axial output signals in response to the portions of the signals received by elements 26, 28. The axial output signals are transmitted to controller 18. Referring to FIG. 2C, element 30 is configured to generate a radial ultrasound signal that travels in a substantially radial direction towards axis 32 and into bony member 12. As used herein a "substantially radial direction" means that the signals travel in a direction that is nearer to being parallel to a line extending perpendicular to axis 32 than to being parallel to axis 32. Portions of this signal are reflected by bony member 12 in a direction away from axis 32 and element 30 is further configured to receive portions of the radial ultrasound signal after reflection by bony member 12 and to generate a pulse-echo output signal in response. The pulse-echo output signal is transmitted to controller 18. In the illustrated embodiment, a single transducer 16 houses elements 22, 24, 26, 28, 30. It should be understood, however, that the elements could alternatively be housed in multiple transducers. For example, in one embodiment, one transducer may contain the elements 22, 24, 26, 28 used to transmit and receive signals sent along axis 32 while another transducer may contain the element 30 used to transmit and receive signals travelling radially relative to axis 32. In either embodiment, the axial and radial ultrasound signals are directed at the same site. It should also be understood that, although elements 22, 24, 26, 28 are referenced only as transmitting or receiving in the illustrated embodiment, any of elements 22, 24, 26, 28 could be configured to both transmit and receive ultrasound signals.

Controller 18 controls the generation of ultrasound signals from transducer 16 and processes signals received by transducer 16 to generate an estimate of a characteristic of the bone tissue in bony member 12. Controller 18 may comprise a programmable microprocessor or microcontroller or may comprise an application specific integrated circuit (ASIC). Controller 18 may include signal generating and processing circuitry that powers transducer 16 with electronic pulses and digitizes the received waveforms from transducer 16. In certain embodiments, controller 18 may include a memory and a central processing unit (CPU). Controller 18 may also include an input/output (I/O) interface including a plurality of input/output pins or terminals through which the controller 18 may receive a plurality of input signals and transmit a plurality of output signals. The input signals may include the axial output signals received from elements 26, 28 of transducer 16 and the pulse-echo output signal received from element 30 of transducer 16. The output signals may include control signals used to cause elements 22, 24 and 30 to generate ultrasound signals used in interrogating bony member 12. The output signals may also include signals indicative of parameters associated with the signals received from elements 26, 28, 30 such as an axial transmission time delay and a pulse-echo time delay as well as signals indicative of characteristics of the bone tissue in bony member 12. Controller 18 may provide these output signals a conventional output device such as a monitor or other display screen.

Figure 3:
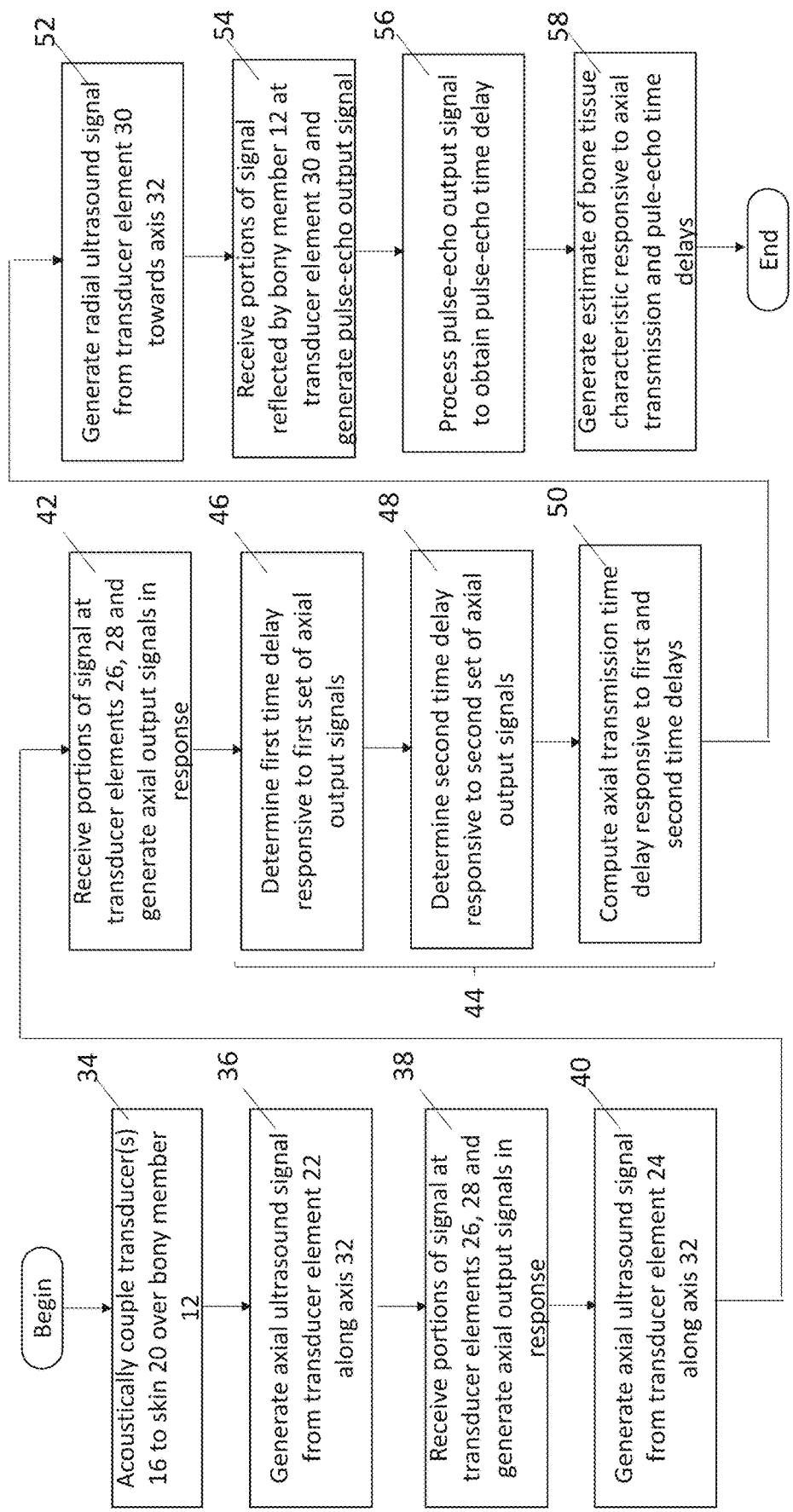
FIG. 3 is a flowchart diagram of a method for non-invasive and quantitative assessment of the status of bone tissue in a bony member in accordance with one embodiment of the present teachings.

Referring now to FIG. 3, controller 18 may be configured with appropriate programming instructions (i.e., software or a computer program) to implement a method for non-invasive and quantitative assessment of the status of bone tissue in a bony member, such as bony member 12, within living organism, such as living organism 14. The method may begin with the step 34 acoustically coupling transducer 16 to skin 20 disposed over the bony member 12. In accordance with conventional practice a coupling gel may be disposed between the transducer 16 and skin 20. The method may continue with the step 36 of generating an axial ultrasound signal from transducer 16 towards and into bony member 12. Referring to FIG. 2A, the axial ultrasound signal may be generated from element 22 of transducer 16. Portions of the axial ultrasound signal travel along axis 32 of bony member 12 in one axial direction. Referring again to FIG. 3, the method may continue with the step 38 of receiving portions of the axial ultrasound signal at a pair of acoustic elements 26, 28 of transducer 16 after those portions exit bony member 12 and generating a pair of axial output signals in response. Referring again to FIG. 2A, portions of the signal exit bony member 12 after travelling along axis 32 and are received by elements 26, 28 of transducer 16. Elements 26, 28 generate axial output signals in response that are provided to controller 18.

Referring again to FIG. 3, in some embodiments the method may continue with the step 40 of generating another axial ultrasound signal from transducer 16 towards and into bony member 12. Referring to FIG. 2B, the axial ultrasound signal may be generated from element 24 of transducer 16. Portions of the axial ultrasound signal travel along axis 32 of bony member 12 in another axial direction opposite to the direction traversed by the signal generated from element 22 in step 36. Referring again to FIG. 3, the method may continue with the step 42 of receiving portions of the axial ultrasound signal at a pair of acoustic elements 26, 28 of transducer 16 after those portions exit bony member 12 and generating another pair of axial output signals in response. Referring again to FIG. 2B, portions of the signal exit bony member 12 after travelling along axis 32 and are received by elements 26, 28 of transducer 16. Elements 26, 28 generate additional axial output signals in response that are provided to controller 18. In the illustrated embodiment, the same acoustic elements 26, 28 receive portions of the axial ultrasound signals generated by elements 22, 24. In an alternate embodiment transducer 16 may include multiple pairs of acoustic elements similar to elements 26, 28 with one pair receiving portions of the signal generated by element 22 and another pair receiving portions of the signal generated by element 24.

Figure 4:
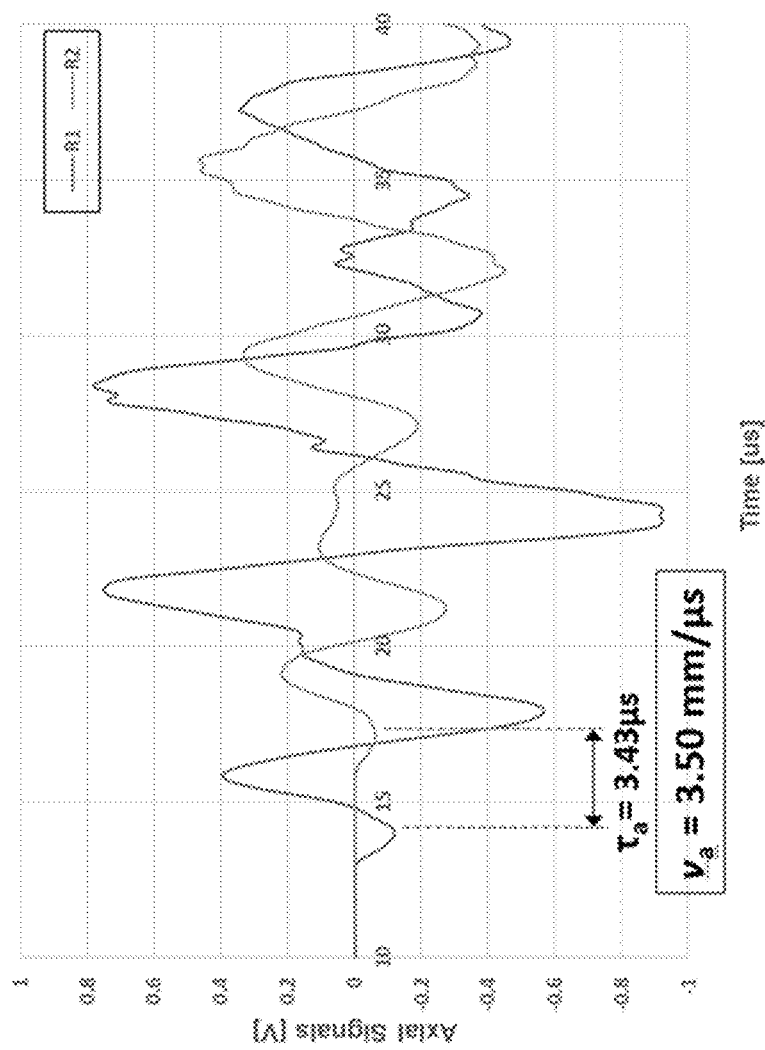
FIG. 4 is a timing diagram showing output signals from a transducer of the system of FIG. 1 following propagation of an ultrasound signal along a longitudinal axis of a bony member.

Referring again to FIG. 3, the method may continue with the step 44 of processing each pair of axial output signals generated by elements 26, 28 to obtain an axial transmission time delay. As noted above, some embodiments may include a single pair of axial output signals while other embodiments may include multiple pairs of axial output signals. Referring to FIG. 4, a comparison of a pair of signals output by elements 26, 28 can be used to determine an axial transit time $\tau a$ through bony member 12. In particular, controller 18 can determine a difference in time between predetermined portions of the signals generated by elements 26, 28 such as a peak/amplitude or a zero crossing. Controller 18 can further determine an axial ultrasound velocity Va responsive to the axial transit time $\tau a$ and a distance between elements 26, 28 in accordance with the following formula: $Va=d/\tau a$. Referring again to FIG. 3, in accordance with one embodiment in which multiple pairs of axial output signals are obtained, step 44 may include several substeps. In substep 46, controller 18 may determine a first time delay responsive to the axial output signals generated by elements 26, 28 responsive to the axial ultrasound signal generated by element 22. In substep 48, controller 18 may determine a second time delay responsive to the axial output signals generated by elements 26, 28 responsive to the axial ultrasound signal generated by element 24. In substep 50, controller 18 computes the axial transmission time delay responsive to the first and second time delays. In one embodiment, controller 18 may compute the axial transmission time delay by averaging the first and second time delays.

Figure 5:
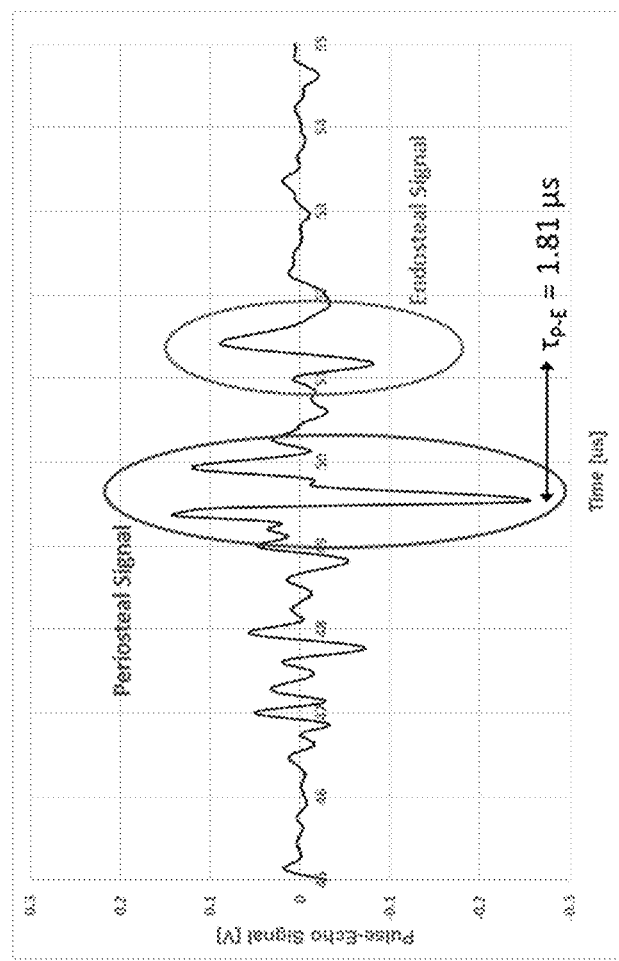
FIG. 5 is a timing diagram showing an output signal from the transducer of the system of FIG. 1 following reflection of an ultrasound signal away from the longitudinal axis of the bony member.

Referring again to FIG. 3, the method may continue with the step 52 of generating a radial ultrasound signal from transducer 16 towards and into bony member 12. Referring to FIG. 2C, element 30 of transducer 16 generates the radial ultrasound signal and directs the signal towards axis 32 of bony member 12. Portions of the radial ultrasound signal are reflected by bony member 12 in a direction away from axis 32 and back towards element 30. A first portion of the radial ultrasound signal will be reflected by the periosteum of bony member 12. A second portion of the radial ultrasound signal will be reflected by the endosteum of bony member 12. Referring again to FIG. 3, the method may continue with the step 54 of receiving the portions of the radial ultrasound signal reflected by bony member 12 and generating a pulse-echo output signal in response. Thereafter, the method may continue with the step 56 of processing the pulse-echo output signal to obtain a pulse-echo time delay. Referring to FIG. 5, an exemplary pulse-echo output signal is shown.

Controller 18 is configured to recognize portions of the pulse-echo output signal corresponding to the portions of the radial ultrasound signal reflected by the periosteum and endosteum. A comparison of the two portions of the pulse-echo output signal output by element 30 can be used to determine a pulse-echo transit time $\tau p$–E from bony member 12. In particular, controller 18 can determine a difference in time between predetermined portions of the signals generated by element 30 such as a peak/amplitude or a zero crossing. Finally, controller 18 may determine a nominal cortical thickness CTn of the bony member 12 in accordance with the following formula: $CTn=Va*\tau p-E$. Note that CTn is considered to be nominal since the axial ultrasound velocity Va and radial ultrasound velocity Vr are not generally equal to each other, but nevertheless are widely assumed to be related linearly by $Vr=\alpha*Va$, where a is a positive number less than or equal to one. It should be understood, therefore, that the information contained in CTn is equivalent to that contained in the actual cortical thickness, CT, where $CT=Vr*\tau p-E$.

Referring again to FIG. 3, the method may continue with the step 58 of generating an estimate of a characteristic of the bone tissue in bony member 12 responsive to the axial-transmission time delay and the pulse-echo time delay. The characteristic may, for example, comprise one or more of bone-mineral density, bone mass, cortical thickness, cross-sectional area, medullar thickness, bone width, bone geometry, bone strength or bone fracture risk. This information may be used in the assessment of osteoporosis or osteoporotic fracture risk-including of bones distinct from the bony member 12 subjected to the ultrasound signals. For example, information from interrogation of the tibia may be used to assess fracture risk in the hip, spine or other bones. In making the assessment, controller 18 may implement various pattern recognition techniques, both linear and non-linear, and including neural networks as well as discussed in Duda, Richard O. et al. "Pattern Classification (Pt. 1) $2^{nd}$ ed. (John Wiley and Sons, 2001) which is incorporated herein by reference. Controller 18 may further implement deep learning and other statistical learning techniques. The measurement of both the axial-transmission time delay and the pulse-echo time delay allows for identification of both bone quality and cortical thickness—both of which are related to bone strength and fracture risk. In particular, the axial-transmission time delay and the pulse-echo time delay can be used in a classification scheme (see FIG. 7) to identify individuals at greatest risk of a fragility fracture.

Figure 7:
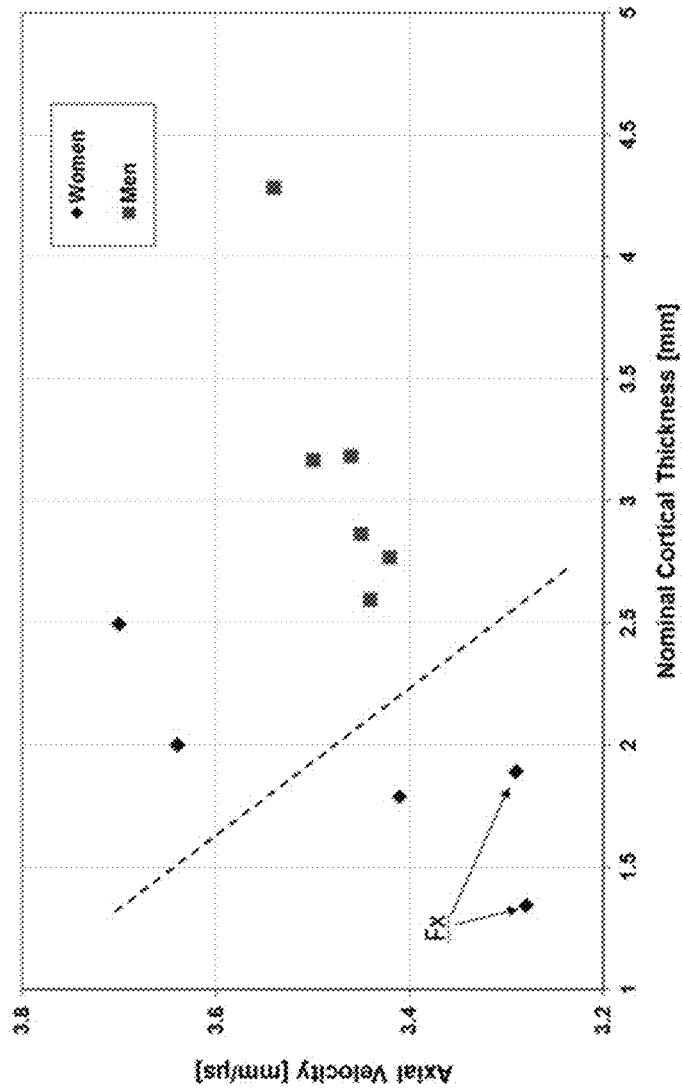
FIG. 7 is a graph summarizing the results of testing of a system and method or non-invasive and quantitative assessment of the status of bone tissue in a bony member in accordance with the present teachings.

Referring now to FIGS. 6-7, the results of testing of a system and method in accordance with the present teachings will be described. Applicant used the system and method on a group of 11 subjects. Referring to FIG. 6, the subjects varied in age from 21-72 with a mean age of 46. The subjects had a racial composition of ninety-one (91) percent Caucasian (white) and nine (9) percent Asian. The subjects included six (6) males and five (5) females. The subjects varied in height from one hundred and fifty (150) centimeters to one hundred and seventy-five (175) centimeters with a mean of one hundred and sixty-two (162) centimeters. The subjects varied in weight from forty-seven (47) kilograms to seventy-seven (77) kilograms with a mean of fifty-nine (59) kilograms. When tested, the system generated an axial ultrasound velocity Va of between 3.28 and 3.70 mm/us with a mean of 3.47 mm/us and a pulse echo transit time $\tau p$=E of between 0.82 and 2.42 us with a mean of 1.49 us. The pulse-echo transit time $\tau p$–E was used to generate a nominal cortical thickness CTn as described above and the subjects were plotted along a graph of axial velocity Va vs. nominal cortical thickness CTn as shown in FIG. 7. Each data point was found to be located in a distinct region (i.e., a hypothesized distinct bone quality-bone structural state) of the quadrant associated with axial ultrasound velocity Va and nominal cortical thickness CTn. The notation Fx indicates the two subjects with fragility fractures. A hypothetical (dashed) line is shown hypothesizing an "optimal" fracture risk class segmentation.

A system and method for non-invasive and quantitative assessment of the status of bone tissue in a bony member within a living organism in accordance with the present teachings are advantageous relative to conventional systems and methods because the inventive system and method use multiple modes of ultrasound interrogation to provide the most accurate information on both bone quality and cortical thickness thereby providing an improved assessment of bone strength and fracture risk. In this manner, the system and method will allow primary care physicians to better assess fracture risk to reduce under-diagnosis of osteoporosis and thereby reduce fragility fractures and associated morbidities.

While the invention has been shown and described with reference to one or more particular embodiments thereof, it will be understood by those of skill in the art that various changes and modifications can be made without departing from the spirit and scope of the invention.

I claim:

1. A system for non-invasive and quantitative assessment of the status of bone tissue in a bony member within a living organism, comprising:
   a transducer configured for coupling to skin disposed over the bony member;
   a controller coupled to the transducer and configured to:
      generate a first control signal causing the transducer to
         generate a first axial ultrasound signal from the transducer towards and into the bony member wherein portions of the first axial ultrasound signal travel along a longitudinal axis of the bony member in a first axial direction;
         receive first and second portions of the first axial ultrasound signal at a first pair of acoustic elements of the transducer after the first and second portions of the first axial ultrasound signal have exited the bony member and generate a first pair of axial output signals in response;
      process the first pair of axial output signals to obtain an axial transmission time delay;
      generate a second control signal causing the transducer to
         generate a first radial ultrasound signal from the transducer towards and into the bony member wherein portions of the first radial ultrasound signal are reflected by the bony member in a direction away from the longitudinal axis of the bony member;
         receive first and second portions of the first radial ultrasound signal after reflection by the bony member and generate a pulse-echo output signal in response;
      process the pulse-echo output signal to obtain a pulse-echo time delay corresponding to a transit time for the first radial ultrasound signal to travel between a periosteum of the bony member and an endosteum of the bony member; and,
      generate an estimate of a characteristic of the bone tissue responsive to the axial-transmission time delay and the pulse-echo time delay.

2. The system of claim 1 wherein the controller is further configured to
   generate a third control signal causing the transducer to
      generate a second axial ultrasound signal from the transducer towards and into the bony member wherein portions of the second axial ultrasound signal travel along the longitudinal axis of the bony member in a second axial direction;
      receive first and second portions of the second axial ultrasound signal at a second pair of acoustic elements of the transducer after the first and second portions of the second axial ultrasound signal have exited the bony member and generate a second pair of axial output signals in response;
   process the first and second pairs of axial output signals to obtain the axial transmission time delay.

3. The system of claim 2 wherein the second pair of acoustic elements is the first pair of acoustic elements.

4. The system of claim 2 wherein the second pair of acoustic elements differs from the first pair of acoustic elements.

5. The system of claim 2 wherein the controller is further configured, in processing the first and second pairs of axial output signals, to:
   determine a first time delay responsive to the first pair of axial output signals;
   determine a second time delay responsive to the second pair of axial output signals; and,
   compute the axial transmission time delay responsive to the first time delay and the second time delay.

6. The system of claim 5 wherein the controller is further configured, in computing the axial transmission time delay, to average the first time delay and the second time delay.

7. The system of claim 1 wherein the first portion of the first radial ultrasound signal is reflected by the periosteum of the bony member and the second portion of the first radial ultrasound signal is reflected by the endosteum of the bony member.

8. A system for non-invasive and quantitative assessment of the status of bone tissue in a bony member within a living organism, comprising:
   a first transducer configured for coupling to skin disposed over the bony member;
   a second transducer configured for coupling to skin disposed over the bony member;
   a controller coupled to the first and second transducers and configured to:
      generate a first control signal causing the first transducer to
         generate a first axial ultrasound signal from the first transducer towards and into the bony member wherein portions of the first axial ultrasound signal travel along a longitudinal axis of the bony member in a first axial direction;
         receive first and second portions of the first axial ultrasound signal at a first pair of acoustic elements of the first transducer after the first and second portions of the first axial ultrasound signal have exited the bony member and generate a first pair of axial output signals in response;
      process the first pair of axial output signals to obtain an axial transmission time delay;
      generate a second control signal causing the second transducer to
         generate a first radial ultrasound signal from the second transducer towards and into the bony member wherein portions of the first radial ultrasound signal are reflected by the bony member in a direction away from the longitudinal axis of the bony member;

receive first and second portions of the first radial ultrasound signal after reflection by the bony member and generate a pulse-echo output signal in response;

process the pulse-echo output signal to obtain a pulse-echo time delay corresponding to a transit time for the first radial ultrasound signal to travel between a periosteum of the bony member and an endosteum of the bony member; and, generate an estimate of a characteristic of the bone tissue responsive to the axial-transmission time delay and the pulse-echo time delay.

9. The system of claim 8 wherein the controller is further configured to generate a third control signal causing the first transducer to generate a second axial ultrasound signal from the first transducer towards and into the bony member wherein portions of the second axial ultrasound signal travel along the longitudinal axis of the bony member in a second axial direction;

receive first and second portions of the second axial ultrasound signal at a second pair of acoustic elements of the first transducer after the first and second portions of the second axial ultrasound signal have exited the bony member and generate a second pair of axial output signals in response;

process the first and second pairs of axial output signals to obtain the axial transmission time delay.

10. The system of claim 9 wherein the second pair of acoustic elements is the first pair of acoustic elements.

11. The system of claim 9 wherein the second pair of acoustic elements differs from the first pair of acoustic elements.

12. The system of claim 9 wherein the controller is further configured, in processing the first and second pairs of axial output signals, to:

determine a first time delay responsive to the first pair of axial output signals;

determine a second time delay responsive to the second pair of axial output signals; and, compute the axial transmission time delay responsive to the first time delay and the second time delay.

13. The system of claim 12 wherein the controller is further configured, in computing the axial transmission time delay, to average the first time delay and the second time delay.

14. The system of claim 8 wherein the first portion of the first radial ultrasound signal is reflected by the periosteum of the bony member and the second portion of the first radial ultrasound signal is reflected by the endosteum of the bony member.

15. A method of non-invasive and qualitative assessment of the status of bone tissue in a bony member within a living organism, comprising the steps of:

acoustically coupling a transducer to skin disposed over the bony member;

generating a first axial ultrasound signal from the transducer towards and into the bony member wherein portions of the first axial ultrasound signal travel along a longitudinal axis of the bony member in a first axial direction;

receiving first and second portions of the first axial ultrasound signal at a first pair of acoustic elements of the transducer after the first and second portions of the first axial ultrasound signal have exited the bony member and generating a first pair of axial output signals in response;

processing the first pair of axial output signals to obtain an axial transmission time delay;

generating a first radial ultrasound signal from the transducer towards and into the bony member wherein portions of the first radial ultrasound signal are reflected by the bony member in a direction away from the longitudinal axis of the bony member;

receiving first and second portions of the first radial ultrasound signal after reflection by the bony member and generating a pulse-echo output signal in response;

processing the pulse-echo output signal to obtain a pulse-echo time delay corresponding to a transit time for the first radial ultrasound signal to travel between a periosteum of the bony member and an endosteum of the bony member; and, generating an estimate of a characteristic of the bone tissue responsive to the axial-transmission time delay and the pulse-echo time delay.

16. The method of claim 15, further comprising the steps of generating a second axial ultrasound signal from the transducer towards and into the bony member wherein portions of the second axial ultrasound signal travel along the longitudinal axis of the bony member in a second axial direction;

receiving first and second portions of the second axial ultrasound signal at a second pair of acoustic elements of the transducer after the first and second portions of the second axial ultrasound signal have exited the bony member and generating a second pair of axial output signals in response;

wherein processing the first pair of axial output signals includes processing the first and second pairs of axial output signals to obtain the axial transmission time delay.

17. The method of claim 16 wherein the second pair of acoustic elements is the first pair of acoustic elements.

18. The method of claim 16 wherein the second pair of acoustic elements differs from the first pair of acoustic elements.

19. The method of claim 16 wherein processing the first and second pairs of axial output signals includes determining a first time delay responsive to the first pair of axial output signals;

determining a second time delay responsive to the second pair of axial output signals; and computing the axial transmission time delay responsive to the first time delay and the second time delay.

20. The method of claim 19 wherein computing the axial transmission time delay includes averaging the first time delay and the second time delay.

21. The method of claim 15 wherein the first portion of the first radial ultrasound signal is reflected by the periosteum of the bony member and the second portion of the first radial ultrasound signal is reflected by the endosteum of the bony member.

22. A method of non-invasive and qualitative assessment of the status of bone tissue in a bony member within a living organism, comprising the steps of:

acoustically coupling a first transducer to skin disposed over the bony member;

generating a first axial ultrasound signal from the first transducer towards and into the bony member wherein portions of the first axial ultrasound signal travel along a longitudinal axis of the bony member in a first axial direction;

receiving first and second portions of the first axial ultrasound signal at a first pair of acoustic elements of the first transducer after the first and second portions of the first axial ultrasound signal have exited the bony member and generating a first pair of axial output signals in response;

processing the first pair of axial output signals to obtain an axial transmission time delay;

acoustically coupling a second transducer to skin disposed over the bony member;

generating a first radial ultrasound signal from the second transducer towards and into the bony member wherein portions of the first radial ultrasound signal are reflected by the bony member in a direction away from the longitudinal axis of the bony member;

receiving first and second portions of the first radial ultrasound signal after reflection by the bony member and generating a pulse-echo output signal in response;

processing the pulse-echo output signal to obtain a pulse-echo time delay corresponding to a transit time for the first radial ultrasound signal to travel between a periosteum of the bony member and an endosteum of the bony member; and, generating an estimate of a characteristic of the bone tissue responsive to the axial-transmission time delay and the pulse-echo time delay.

23. The method of claim 22, further comprising the steps of:

generating a second axial ultrasound signal from the first transducer towards and into the bony member wherein portions of the second axial ultrasound signal travel along the longitudinal axis of the bony member in a second axial direction;

receiving first and second portions of the second axial ultrasound signal at a second pair of acoustic elements of the first transducer after the first and second portions of the second axial ultrasound signal have exited the bony member and generating a second pair of axial output signals in response;

wherein processing the first pair of axial output signals includes processing the first and second pairs of axial output signals to obtain the axial transmission time delay.

24. The method of claim 23 wherein the second pair of acoustic elements is the first pair of acoustic elements.

25. The method of claim 23 wherein the second pair of acoustic elements differs from the first pair of acoustic elements.

26. The method of claim 23 wherein processing the first and second pairs of axial output signals includes
determining a first time delay responsive to the first pair of axial output signals;
determining a second time delay responsive to the second pair of axial output signals; and
computing the axial transmission time delay responsive to the first time delay and the second time delay.

27. The method of claim 26 wherein computing the axial transmission time delay includes averaging the first time delay and the second time delay.

28. The method of claim 22 wherein the first portion of the first radial ultrasound signal is reflected by the periosteum of the bony member and the second portion of the first radial ultrasound signal is reflected by the endosteum of the bony member.

29. A method of non-invasive and quantitative assessment of the status of bone tissue in a bony member within a living organism, comprising the steps of:

acoustically coupling a transducer to skin disposed over the bony member;

generating a first axial-ultrasound signal in the bony member along a longitudinal axis of the bony member in a first axial direction to obtain a first pair of axial-ultrasound output signals, and generating a second axial-ultrasound signal in the bony member along the longitudinal axis of the bony member in a second axial direction, wherein the second axial direction is opposite to the first axial direction, to obtain a second pair of axial-ultrasound output signals;

processing the first pair of axial-ultrasound output signals and the second pair of axial-ultrasound output signals, to obtain an axial-transmission time delay;

generating a radial ultrasound signal and directing the radial ultrasound signal from the transducer radially through the bone tissue to obtain a pulse-echo output signal;

processing the pulse-echo output signal to obtain a pulse-echo time delay corresponding to a transit time for the radial ultrasound signal to travel between a periosteum of the bony member and an endosteum of the bony member; and, generating an estimate of a characteristic of the bone tissue responsive to both the axial-transmission time delay and the pulse-echo time delay.

* * * * *